United States Patent [19]

Levin

[11] Patent Number: 5,676,973
[45] Date of Patent: Oct. 14, 1997

[54] TOPICAL COMPOSITIONS CONTAINING LYCD AND FLUOROURACIL

[76] Inventor: Robert H. Levin, 11127 Jardin Pl., Cincinnati, Ohio 45241

[21] Appl. No.: 640,700

[22] Filed: May 1, 1996

Related U.S. Application Data

[62] Division of Ser. No. 703,917, May 22, 1991, Pat. No. 5,514,591, which is a division of Ser. No. 503,225, Apr. 2, 1990, Pat. No. 5,023,090, which is a continuation-in-part of Ser. No. 394,862, Aug. 16, 1989, Pat. No. 4,942,031, which is a continuation-in-part of Ser. No. 159,390, Feb. 23, 1988, abandoned.

[51] Int. Cl.$^6$ ..................................................... A61K 35/72
[52] U.S. Cl. ........................ 424/520; 424/195.1; 514/50
[58] Field of Search ................................ 424/520, 195.1; 514/50

[56] References Cited

PUBLICATIONS

The Merck Manuel of Diagnosis and Therapy, Merck Research Laboratories, Rahway, NJ, 1992, pp. 2457 and 2499 1992.

Poydock et al., Experimental Cell Biology 46: 231–239 (1978).

Cook et al., Journal of Surgical Oncology 7(5):337–345 (1975).

Fardon et al., Journal of Surgical Oncology 10(1): 10–21 (1978).

*Primary Examiner*—Jean C. Witz
*Attorney, Agent, or Firm*—Samuel Kurlandsky

[57] ABSTRACT

A topical composition comprising LYCD together with known topically active useful medicinal agents such as antiwrinkling, antibiotic, anticancer, antifungal, antiinflammatory such as anti-acne, antiviral, wound healing, and hair-growing agents. The LYCD works together with the other active agents to achieve a synergistic result more effective than can be obtained from the topical agents individually, and more effective than could be predicted from the mere addition of the known efficacies of the individual ingredients.

4 Claims, No Drawings

TOPICAL COMPOSITIONS CONTAINING LYCD AND FLUOROURACIL

RELATED APPLICATION

The present application is a Divisional application of U.S. application Ser. No. 07/703,917, filed May 22, 1991, now U.S. Pat. No. 5,514,591, which is a division of application Ser. No. 07/503,225, filed Apr. 2, 1990, now U.S. Pat. No. 5,023,090, issued Jun. 11, 1991; which is a continuation-in-part of application Ser. No. 97/394,862, filed Aug. 16, 1989, now U.S. Pat. No. 4,942,031, issued Jul. 17, 1990; which is a continuation-in-part of application Ser. No. 07/159,390, filed Feb. 23, 1988, now abandoned.

BACKGROUND OF THE INVENTION

1. Field of the Invention

The present invention relates to topically applied medicinal compositions, and more particularly refers to such compositions having active topical medicinal ingredients, and additionally having LYCD in amounts sufficient to act with the other active ingredients to provide synergistic therapeutic results.

2. Description of the Prior Art

LYCD as utilized herein in the specification and claims is the acronym for Live Yeast Cell Derivative. The material is also known as Skin Respiratory Factor (SRF), Tissue Respiratory Factor (TRF), and Procytoxoid (PCO). The product, LYCD, is an alcoholic extract of viable *Saccharomyces cerevisiae*. The material is produced and marketed by MDH Laboratories, Inc., Cincinnati, Ohio 45210 as a standard article of commerce. Another producer of LYCD is Universal Foods Corporation, Fermentation Division, Milwaukee, Wis. 53202. LYCD is available for experimental use as a bulk drug assaying 5 units to 40 units/mg of respiratory activity. In topical medicinal preparations it is characterized and quantified in terms of Skin Respiratory Factor (SRF) units. A unit of activity is calculated as the amount of SRF which is required to increase the oxygen uptake of 1 mg of dry weight rat abdominal skin by 1 percent at the end of a 1 hour testing period in a Warburg apparatus.

LYCD is also available as LYCODERM® ointment containing 2,000 units Skin Respiratory Factor (SRF) per ounce, from Arel Pharmaceuticals, Inc., Cincinnati, Ohio. In the prior art the well known hemorrhoidal ointment, PREPARATION H®, contains 2000 units of SRF (ca 1%) per ounce of ointment.

J. Z Kaplan (Arch. Surge. 119(9) p. 1005–8 (1984) has reported that, in a double blind human skin graft study donor sites treated with LYCD ointment, statistically significant earlier angiogenesis and epitheliazation occurred as compared with donor sites in the same patients treated with ointment bases (without LYCD). This study confirmed earlier laboratory reports such as that of Wm. Goodson et. al. Journal of Surgical Research 21: 125–129 (1976) showing that LYCD is capable of stimulating wound oxygen consumption, epitheliazation, and collagen synthesis.

As reported in the Cincinnati Inquirer of Dec. 12, 1986, Ashlley Hunter Cosmetic Co. offers a facial cream containing LYCD to minimize wrinkles.

For milder forms of acne, which may be inflammatory, topical benzoyl peroxide (BP), an antibacterial and oxidizing agent, topical erythromycin (EM), clindamycin phosphate (CP), oral tetracyclines, or EM antibiotics are usually effective treatments, as disclosed in the prior art. (C. D. Bunker, Drugs Today, 24, 229 (1988).

SUMMARY OF THE INVENTION

It is an object of the present invention to provide topically applied pharmaceutical compositions suitable for the treatment of various ailments and physical conditions of the skin such as acne, bed sores, burns, infections, trauma, ulcers, wounds, and wrinkles.

It is a further object to provide compositions of the type described which are more effective than compositions presently known in the art.

It is a prime object of the invention to provide topical compositions of the type described for the treatment of acne, and more particularly, severe forms of acne, which compositions are more effective as remedies than the compositions presently known and used in the art.

The foregoing and other objects, advantages and characterizing features will become apparent from the following description of certain illustrative embodiments of the invention.

According to the invention, pharmaceutical compositions for topical application are provided by utilizing LYCD in combination with known pharmaceutical agents or remedies. The LYCD acts synergistically with the other agents to provide a composition having greater effectiveness than that of the individual agents, and a greater effectiveness than could be predicted by combining (in an additive fashion) the known or theoretical effectiveness of the individual ingredients.

According to the invention, it has been further found that many patients with severe acne, refractory to even long term treatment with a variety of the conventional acne remedies experience significant improvement in their acne condition within thirty days when treated twice daily with a combination of any of the conventional antibacterial acne medications and LYCD.

It has been additionally found that mild to moderately severe acne can be treated and the condition ameliorated by the application of a topical pharmaceutical composition comprising LYCD in a suitable vehicle, even in the absence of conventional acne remedies.

DESCRIPTION OF THE PREFERRED EMBODIMENTS

LYCD, Live Yeast Cell Derivative, also known as SRF or TRF, is a commercial material produced by the method set forth in U.S. Pat. Nos. 2,239,345, 2,320,478, and 2,320,479. Which are herein incorporated by reference, and is standardized as units with 1 unit (U) of SRF increasing the uptake of oxygen by minced rat abdominal skin (1 mg. dry weight) by 1% in a 1-hour measurement by Warburg manometry.

EXAMPLE 1

The compositions of the invention may be produced by either of two general methods. In the first method, for example, an ointment composition may be formulated by mixing LYCD with conventional ointment-forming ingredients. One such ointment composition is LYCODERM®. A registered trademark material marketed by Arel Pharmaceuticals, Cincinnati, Ohio, having the following compositions:

|  | Per 100 Parts |
| --- | --- |
| Beeswax | 4.0 |
| Lanolin | 4.0 |
| Petrolatum | 87.9 |
| Shark liver oil | 3.0 |
| Phenyl mercuric nitrate | 0.01 |
| LYCD (2000) SRF units/ounce) | 1.0 approx. |
| Thyme oil | 0.1 |

PROCEDURE

In preparing the above compositions, the beeswax, petrolatum, shark liver oil and phenyl mercuric nitrate are treated together to a temperature of 140 deg. F. in a steam-jacketed s.s. kettle. The materials are mixed until the mixture is uniform. Then the steam is turned off and cooling water is introduced while mixing is continued. When the mixture has reached a temperature of 110 deg. F., the LYCD and thyme oil are added. When the composition becomes uniform, mixing is stopped. Filling may be carried out at temperatures of between 90 and 110 deg. F.

In utilizing the first method of producing the compositions of the invention, the LYCODERM® ointment as produced above but utilizing 200 to 1800 SRF units per ounce of formulation is mixed with the known pharmaceutical agent by a conventional method.

The second method of carrying out the present invention comprises mixing bulk LYCD into the conventional pharmaceutical composition.

In general, it has been found that effective compositions are formulated using LYCD concentrations in the range of about 0.1% to 0.5% by weight of the composition, constituting, for example, 10% to 50% of that employed in the basic LYCODERM® ointment formulation. This translates into 200 to 1000 LYCD or SRF units per ounce of combined product. Stated in another way, the new compositions have a LYCD concentration of approximately 0.1% to 0.5% compared with approximately 1.0% LYCD in the basic LYCODERM® formulation. However, for certain compositions LYCD in the amount of 0.8% of the total composition produces optimum results.

Correspondingly, the other active components of the new compositions are found to be synergistically efficacious at concentrations in the range of 5% to 50% of that found to be efficacious in marketed pharmaceutical products.

ANTI ACNE COMPOSITIONS

EXAMPLE 2

The above-described LYCODERM® ointment was formulated using 1000 units of S RF per ounce. To this formulation was added sufficient 2% erythromycin to yield an ointment containing 0.5% LYCD and 1% erythromycin. In a controlled clinical trial this composition was equally effective in the topical control of acne vulgaris as a conventional 2% ointment preparation of erythromycin. (An example of such a medicinal preparation, NDA 50–584, Akneymycin Topical Ointment, 2%, is a topical erythromycin accepted by the FDA for topical control of acne vulgaris.)

EXAMPLE 3

Alternatively, a marketed anti-acne 2% Erythromycin product was reformulated as follows:

| Erytromycin Base | 1% w/v |
| --- | --- |
| LYCD | 0.5% w/v |
| Alcohol | 55% v/v |
| Oleyl Alcohol | 5% w/v |
| Perfume | q.s. |
| Propylene Glycol | to 100% |

Following the same treatment regimen, the 1% Erythromycin solution containing approximately 0.5% LYCD of Example 2 (assaying 1,000 units of SRF per ounce of formulation) was found to be more effective than a similar 2% Erythromycin solution without LYCD in the treatment of Acne grades 2 and 3 (moderate to severe).

EXAMPLE 4

In an analogous fashion, Lincomycin Hydrochloride or Clindamycin Phosphate at a concentration of 0.5% is combined with 0.5% LYCD in the LYCODERM® formulation to provide an ointment as effective in treating common acne as the conventional 1% Clindamycin Phosphate topical medication, and more effective than either agent individually or predictable in their combination.

EXAMPLE 5

Ten patients suffering with severe acne completely refractory to months of prior treatment with a variety of conventional acne medications were treated with an admixtured combination of Cleocin T (clindamycin phosphate solution) and LYCODERM® Ointment. The final formulation contained approximately 0.34% clindamycin and 0.56% LYCD. Each subject applied this formulation twice daily for 30 days with the following results:

Patient 1: female, age 16: Refractory to Acromycin, Erythrocin, diet, local treatment. The patient was subsequently treated with the low dose combination product of Example 5, and as a result experienced 80% improvement.

Patient 2: male, age 25: Refractory to Achromycin, curattage, Acutane. The patient was then treated with the low dose combination product of Example 5, and as a result experienced 90% improvement.

Patient 3: male, age 30: Refractory to proprietary medicines, Erythromycin, Achromycin, Fostex (10% Benzoyl Peroxide). The patient was then treated with the low dose combination product of Example 5, and experienced 50% improvement.

Patient 4: female, age 21: Refractory to astringents, Erythromycin, and diet. The patient was then treated with the low dose combination product of Example 5, and experienced 85% improvement.

Patient 5: Female, age 18: Refractory to Achromycin, diet, and astringents. The patient was subsequently treated with the low dose formulation of Example 5, and experienced almost 100% improvement.

Patient 6: female, age 24: Refractory to Achromycin, curettage, and diet. The patient was subsequently treated with the low dose formulation of Example 5, and experienced 85% improvement.

Patient 7: Female, age 24: Refractory to Achromycin, diet, local Rx, and proprietary drugs. The patient was subsequently treated with the low dose formulation product of Example 5, and experienced 85% improvement.

Patient 8: Female, age 29: Refractory to Vitamin A ointment, diet, and Achromycin. The patient was subsequently treated with the low dose formulation of Example 5, and experienced 80% improvement.

Patient 9: Male, age 30: Refractory to Achromycin, local Rx, and Acutane: The patient was subsequently treated with the low dose formulation of Example 5, and experienced 80% improvement.

Patient 10: Female, age 20: Refractory to Achromycin, and coal tar products. The patient was subsequently treated with the low dose formulation of Example 5, and experienced 85% improvement.

EXAMPLE 6

In an analogous fashion topical acne treatment formulations containing 5% or 10% Benzoyl Peroxide anti-acne formulations were admixed with LYCODERM® ointment to provide lower dose Benzoyl Peroxide/LYCD combination products more effective than the higher concentration of Benzoyl Peroxide conventionally used in the treatment of acne vulgaris. Additionally, desquamation, symptoms of burning, and other side effects were less frequent.

EXAMPLE 7

In a further test 1.5 oz. FOSTEX® 5% Benzoyl Peroxide Gel was admixed with 2 oz. LYCD ointment to provide a formulation containing approximately 2% Benzoyl Peroxide and 0.5% LYCD (assaying approximately 1,000 units of SRF per ounce of formulation). Further 1 oz. of CLEARASIL®, 10% benzoyl peroxide anti-acne cream, was admixed with 4 oz. of LYCODERM® ointment to provide a formulation containing approximately 2% benzoyl peroxide and 0.8% LYCD. Both compositions are effective in treating mild to severe acne.

EXAMPLE 8

A LYCODERM® composition is prepared comprising containing 1000 units of SRF per ounce (ca 0.5%) and 0.25% of vitamin A acid to provide a topical ointment composition more effective than the retinoic acid by itself in ameliorating the effects of moderate to severe acne.

EXAMPLE 9

The LYCODERM® formulation was applied for twelve weeks to mild to moderately severe acne afflicted subjects in the absence of conventional drugs used in the treatment of acne. The treatment resulted in a 40% reduction in inflammatory lesions. For clinical testing purposes the same formulation was prepared as a placebo by leaving out the LYCD. During this period the placebo, when applied to similarly afflicted patients proved to be ineffective,

EXAMPLE 10

Various protein/peptide growth factors have been used as topical wound-repair agents. It has now been found that Epidermal Growth Factor (EGF), when used in concentrations of 0.0001% in a suitable topical pharmaceutical formulation is an effective treatment for moderate acne.

Further, according to the method of the present invention, compositions containing 500 units per ounce of LYCD/SRF incorporated into commercial formulations of recombinant/ human Epidermal Growth Factor preparations or their reduction products (containing 0.0001% rh EGF) are synergistically more effective in treating severe acne.

FIRST AID BURN AND WOUND-HEALING COMPOSITIONS

EXAMPLE 11

Several commonly used topical antibiotic preparations are accepted by the FDA for non-prescription (OTC) use to help prevent infection and aid in the healing of minor cuts, burns, and abrasions. One such preparation contains 0.5% neomycin sulfate. The second contains 500 units of bacitracin, 5000 units of polymixin B sulfate, and 0.5% neomycin sulfate per gram of composition. To each of these formulations was added 1000 units of LYCD (approximately 0.5%) per ounce of product. The resulting LYCD antibiotic compositions were synergistically more effective for topical first aid use than the conventional components when used separately.

EXAMPLE 12

In an analogous example, a LYCODERM®/antibiotic combination ointment product was formulated as follows:

| Polysorbate 80 | 2 pounds | 1.00% w/w |
|---|---|---|
| Polymixin (7,700 iu/mg) | 117.02 grams | 0.129% w/w |
| Bacitracin Zinc (690 u/mg) | 656.81 grams | 0.724% w/w |
| Phenyl Mercuric Nitrate | 9 grams | 0.01% w/w |
| LYCD (12 u/mg) | 266.7 grams | 0.50% w.w |
| Deionized water | 4# 7 oz | 2.5% w/w |
| Beeswax (white) | 8# 1 oz | 4.00% w/w |
| Lanolin | 8# 1 oz | 4.00% w/w |
| Petrolatum | 167# 13 oz | 83.93% w/w |
| Shark liver oil | 6# 1 oz. | 3.03% w/w |
| Thyme oil | 90 grams | 0.10% w/w |

PROCEDURE

In preparing the above composition, the first four ingredients were mixed and suspended well. The LYCD is dissolved in the water and mixed well with the first ingredients. The resulting solution was heated to 140° F.

Separately, the third group of ingredients was mixed in a clean container and heated to 160° F. With good mixing the first solution was added to the contents of the container; the thyme oil was then added and the composition permitted to cool to 60°–80° for filling into containers.

The product thus produced is ideal for treating minor cuts, burns, and scratches. It appears to work rapidly and especially well on infants and children, where the ointment formulation functions somewhat like an occlusive dressing.

EXAMPLE 13

A similar LYCODERM®/antibiotic ointment formulation was also prepared using LYCD at a concentration of approximately 1.0% (2000 units SRF/ounce of product. Used twice a day for two to four weeks as an emollient in a group of 10 elderly patients suffering from bed sores, this product resulted in 50 to 100% healing.

Separately, LYCD or LYCODERM® ointment may be incorporated into first aid type bandages or dressings to provide a superior product for burn and wound healing.

EXAMPLE 14

Topical antiinfective compositions for wounds including burns may be provided utilizing LYCD in combination with silver sulfadiazine and a suitable ointment-forming base, or LYCD in combination with povidone-iodine and a suitable ointment-forming base.

Live yeast cell derivative (LYCD) per se increases collagen formation. It is accepted in the art that most agents promoting experimental wound healing appear to act primarily to promote collagen synthesis. Controlled clinical studies of LYCD have demonstrated both clinically and statistically earlier angiogenisis, initiation and completion of epithelialazation, and acceleration of wound healing.

The use of a composition such as LYCODERM® formulated with 2000 units of LYCD per ounce of ointment (about 1.0%), and also containing 3% of shark liver oil has also been shown clinically to promote wound healing, including a range of first, second and third degree burn wounds.

Separately, a number of lymphokine/cytokine proteins have been found which enhance wound healing by directly activating macrophages or indirectly stimulating the skin immune system. More than several dozen of these naturally occurring growth factors have been reported in the literature, but are difficult to isolate and characterize, and may actually overlap in identity. Therapeutic doses, although measured in fractions of milligrams, are very costly.

EXAMPLE 15

Epidermal Growth Factor (EGF) is one such growth factor which has been used topically at a concentration of 0.0001% to accelerate normal wound healing by 15–20 percent. According to the method of the present invention, compositions containing 500 units of LYCD as SRF (approximately 0.25%) and 0.0001% EGF are synergistically more effective in treating chronic epidermal ulcers. Similarly using LYCD at 0.1% to 0.5% concentrations (equivalent to 200–1000 LYCD units per ounce of product) in compositions with Fibroblast Growth Factor (FGF), Platelet-Derived Growth Factor (PDGF), Transforming Growth Factor-alpha (TGF-alpha), Transforming Growth Factor-beta (TGF-beta), or Insulin-like Growth Factor-1 (IGF-1) has provided synergistic wound healing compositions. Both partial and full incisional wounds show synergistic healing patterns. Compositions consisting of several of these growth factors formulated with LYCD as in LYCODERM® also result in synergistically acting wound healing products.

EXAMPLE 16

In the area of surgical incisions and wounds, as for example in Gastrointestinal Surgery, excess scarring of the tissue is a not uncommon side effect resulting in surgical adhesions which may require a second operation for correction.

It has now been found that a 10% sterile isotonic saline solution of LYCD can be used as a final incision lavage in such surgical procedures to minimize scarring during the wound healing process. A range of LYCD concentrations of 1% to 25% may be used; and isotonic lactose as well as sterile water are suitable vehicles for this purpose. Additionally, as previously disclosed herein, the LYCD solution stabilizes other growth factor/lymphokine/cytokine proteins at the 1 to 100 nanogram per ml. concentrations required for therapeutic purposes. Thus, for example, 5 nanograms per ml. each of insulin-like growth factor-1 and platelet derived growth factor are added to the 10% LYCD solution to make a growth factor "cocktail" which, when used as a final lavage, significantly reduces the "adhesion" side effect of many cardiac, neurovascular, and gastrointestinal surgical procedures.

Separately as an adjunct to orthopedic surgery, LYCD, formulated as a 5% sterile solution is combined with one or more of a group of growth factors/cytokines (in concentrations of one to 100 nanograms per ml.) to provide compositions for the acceleration of healing of bone and other hard tissue injury. Representative factors include: Bone Morphogenic Protein, Cartilage-derived Growth Factor, Cartilage Inducement Factor, Connective Tissue Activating Peptide III, Fibroblast Growth Factor-basic, Osteogenic Growth Factor, Osteogenic Protein, Osteogenin, Skeletal Growth Factor, Tissue Inhibitor of Metalloproteinese, Transforming Growth Factor alpha, and Transforming Growth Factor beta.

EXAMPLE 17

In another embodiment of this invention lymphokine/cytokine modulating chemicals, such as Tilorone and its congeners, are formulated into topical wound healing compositions in combination with LYCD. Thus the LYCODERM® formulation previously described is prepared using 1000 units of SRF per ounce (ca 0.5% and 0.1% of Tilorone to produce a synergistically effective ointment for the treatment of severe burn wounds and non-healing epidermal ulcers. Depending on the formulation, Tilorone synergy can be demonstrated at concentrations ranging from 0.01% to 0.5% in epithelial tissue repair experiments.

ANTIFUNGAL COMPOSITIONS

EXAMPLE 18

Topical antifungal compositions are used in the treatment of cutaneous or mucocutaneous mycotic infections caused by Candida species, pathogenic dermatophytes, other yeasts, and various superficial fungal infections of the skin. Tolnaftate USP at the level of 0.5%, when formulated with LYCODERM® containing LYCD at a concentration of 1000 units per ounce (ca 0.5%) provides a synergistic composition more effective than the standard topical antifungal preparation containing 1.0% of Tolnaftate. In an analogous manner, Nystatin USP at a concentration of 50,000 units per gram when formulated with LYCD at the 0.5% concentration, and chlortrimazole 0.25% provided compositions equal in antifungal effectiveness with the topical antifungals used alone at 3 and 4 times the concentration employed in the compositions of the invention.

EXAMPLE 19

In similar manner 30 cc. of clotrimazole solution, USP 1%, was admixed with 3 oz. of LYCODERM® ointment, and the resulting combined formulation used to treat a severe tinea pedis infection in a 70 year old male. With twice a day application into the affected and surrounding skin areas, the infection cleared up within a week.

ANTIVIRAL COMPOSITIONS

EXAMPLE 20

Topical antiviral medicinal agents are licensed by the FDA particularly for the treatment of herpes simplex and herpes genitalis. The agent idoxuridine is marketed as a 0.5% ointment. When formulated as a 0.1% concentration of idoxuridine and 0.5% concentration of LYCD (containing 1000 units SRF per ounce), the topical composition showed synergistic anti-herpes simplex viral activity. Similarly, a topical composition containing 0.5% acyclovir and 0.5% LYCD (containing 1000 units of SRF per ounce of LYCODERM® ointment formulation) gave better results in the treatment of herpes genitalia than would be anticipated from the known antiherpes activities of acyclovir in the absence of LYCD. The antiviral efficacy of topical formulations of alpha, beta, or gamma interferons (used at doses of 3 million to 10 million IU) per 30 ml. solution are also enhanced synergistically by the addition of 0.1% to 0.5% of LYCD representing 200 to 1000 units of SRF per ounce of topical composition.

In laboratory cell culture studies, the effect of LYCD, lymphokines and lymphokine modulating chemicals on vaccinia virus infected monkey kidney BSC-40 cells, or human epidermoid A431 cells was investigated. Vaccinia virus is a DNA virus, as is herpes.

EXAMPLE 21

Pre-treated experiments: Each cell line was pretreated with a candidate antiviral compound for 24 hours, washed, and then infected with low multiplicities of vaccinia. After 24 hours of infection, virus was titered on BSC-40 monolayers. The data is expressed in placque-forming units (PFU); and the results of duplicate experiments averaged.

Post-infection experiments: Vaccinia infected cells were exposed to the test material for 24 hours.

The 24 hour preincubation of BSC-40 cells with 100 to 200 micrograms per ml. of LYCD, followed by vaccinia virus infection resulted in a 30% to 40% reduction in PFU. Higher concentrations of LYCD did not quantitatively change the viral inhibition.

EXAMPLE 22

The immunomodulating drug Tilorone, and two of its analogs, RMI-11567, and RMI-11645 were similarly tested for their ability to induce an antiviral state in BSC-40 cells by pretreatment of the cells for 24 hours. (See Progress in Medicinal Chemistry, vol. 18, pp. 136–190, 1981 for a description of these compounds) In these experiments 2–3 micrograms per ml. of the tilorones resulted in an inhibition of viral growth which peaked at 40%, with RMI 11567 being the most active.

EXAMPLE 23

In analogous experiments, pretreatment with the lymphokines gamma interferon, and Interleukin-I (IL-1) at even lower doses (250 units per ml. and 10 units per ml., respectively) resulted in a 60% to 90% stimulation of viral growth. However, combination of each of these materials with 100 micrograms per ml. of LYCD synergistically reduced or reversed this stimulation.

EXAMPLE 24

Surprisingly, in Post-infection cell culture experiments, 1 microgram per ml. of RMI-11567 and 100 micrograms per ml. of LYCD each separately caused a 30% stimulation in viral growth; however, the combination of RMI-11567 and LYCD resulted, synergistically, in a 15% inhibition of vaccinia growth as measured by plaque forming units (PFU). The percent stimulation/inhibition was calculated by comparing the PFU to concurrent control experiments which did not contain any drug.

EXAMPLE 25

In analogous Post-Infection studies with A431 cells, somewhat similar results were obtained. Thus 8 (standard) units per ml. of alpha or beta Interleukin-I resulted in a slight (3%) inhibition of vaccinia growth as measured by PFU; and 100 micrograms per ml. of LYCD resulted in an 18% inhibition of PFU. The combination of 8 units per ml. of IL-1 and 100 micrograms per ml. of LYCD resulted in a synergistic 32–35% inhibition of viral growth as measured by placque-forming units (PFU).

The experiments described in the examples above demonstrate that in cell culture LYCD has significant antiviral activity which can synergistically enhance the antiviral effects of some lymphokines and lymphokine modulating chemicals.

As more fully described below, a standardized LYCD preparation assaying 12 units of Skin Respiratory Factor (SRF) per mg. was used in the above described cell culture studies.

EXAMPLE 26

The addition of 0.5% fluorouracil to the above-described LYCODERM® ointment formulated with 1000 units of SRF (about 0.5% LYCD) per ounce of product provides a composition for the topical treatment of multiple actinic (solar) keratoses which is synergistically more effective than a conventional topical preparation formulated with 1.0% fluorouracil.

ANTIINFLAMMATORY COMPOSITIONS

EXAMPLE 27

Triethanolamine salicylate (10%) is formulated in lotions and creams to provide a topical external analgesic agent for temporary relief from minor pains of arthritis, rheumatism, and muscular aches. When formulated using 5% of triethanolamine salicylate and 200 to 1800 units SRF per ounce of product (equivalent to approximately 0.1% to 0.8% of LYCD), the new composition was synergistically more effective than the original analgesic product containing 10% of triethanolamine salicylate. In an analogous manner, when LYCODERM® is formulated with non-steroidal antiinflammatory agents such as ibuprofen or its isomers (at a level of 1.0% to 5.0%), the resulting topical compositions have a higher level of topical anti-inflammatory efficacy than that demonstrated by the same preparation of the non-steroidal antiinflammatory agent (NAIA) formulated without LYCD.

The adreno-corticoid steroids demonstrate pleitropic activity in cell culture systems and as topical antiinflammatory agents.

Metabolically, LYCD biological activity at the cellular level in animal and human skin results in an increase in oxygen respiration and cell growth. However, in specific human cell lines including human fibroblasts, the effects are variable.

EXAMPLE 28

A number of standard human cell lines were evaluated and methodology was developed leading to the use of A431 cells, Am Type Culture Collection CLL 1555, as a suitable human cell line to study the effect of LYCD on oxygen respiration and cell growth. In order to facilitate study of the metabolic interaction of LYCD with lymphokines, cytokines, other growth factors, and topically useful therapeutic agents, it was necessary to achieve reproducible base line results in a defined serum-free cell culture medium. Cell respiration was quantified using a Clark oxygen electrode oxygraph apparatus. Experiments were done in duplicate, and cell number measurements were always done in quadruplicate, for any single experiment, the amount of (oxygen) respiratory stimulation or inhibition of a measured number of A431 cells can be correlated with the concentration of added LYCD. Respiration is measured within 6–10 minutes of adding the LYCD and/or other substrates.

A standardized LYCD preparation assaying 12 units of SRF/mg. was used in these studies. In a typical titration of A431 cell respiration it was found that 0.75 to 1.25 mg/ml of LYCD resulted in about a 60% increase in respiration. An LYCD concentration of 0.15 mg/ml gave a 10 to 15% increase in respiration; and 1.50 mg/ml of LYCD resulted in a 20% increase in respiration. Higher concentrations of LYCD resulted in no stimulation of baseline respiration.

EXAMPLE 29

In companion experiments it was determined that 25 to 35 picomolar concentrations of hydrocortisone inhibited A431 respiration, but, when added together with LYCD synergistically doubled the respiratory stimulation of 0.2 mg/ml LYCD from 20% to 40%.

A431 cell growth experiments were compared at seven days using a standard commercial serum-free medium (Gibco DME, Dulbecco's Minimum Essential media) and ITS (5 micrograms/ml each of insulin, transferin and selenium).

It was found that a 0.70 mg/ml of LYCD caused significant and reproducible growth of A431 cells. This concentration of LYCD represents about 12% of the concentration of LYCD found in presently marketed products containing LYCD.

LYCD concentrations of 0.02 mg/ml provided a 30% enhancement in A431 cell growth.

Hydrocortisone has been reported in the literature to be an inhibitor of A431 cell growth.

EXAMPLE 30

A seven day study was made to determine the effect of hydrocortisone on cell growth. It was found that hydrocortisone at the very low concentration of $1 \times 10^{-8}$ mg./ml. inhibits A431 cell growth by 65%. However, it was further surprisingly found that the combination of the hydrocortisone plus 0.75 mg/ml of LYCD enhances cell growth by 200%.

EXAMPLE 31

A LYCODERM®/hydrocortisone ointment combination product for topical antiinflammatory therapy was formulated as follows:

| Ingredient | Amount | % w/w |
|---|---|---|
| Polysorbate 80 | 2 pounds | 1.00 |
| Hydrocortisone Acetate | 1 pound | 0.50 |
| Phenyl Mercuric Nitrate | 9.0 grams | 0.01 |
| LYCD (12 u/mg) | 533.34 grams | 1.0 |
| Deionized water | 2.25 pounds | 2.0 |
| Beeswax (white) | 8 lb. 1 oz. | 4.04 |
| Lanolin | 8 lb. 1 oz. | 4.04 |
| Petrolatum | 168.5 pounds | 84.28 |
| Shark Liver Oil | 6 lb. 1 oz. | 3.03 |
| Thyme Oil | 90 grams | 0.10 |

PROCEDURE

The first 3 ingredients were combined and mixed well. The LYCD was dissolved in water, combined with the first group and mixed well. The third group of ingredients was added to a clean container, heated to 160° F. with good mixing. With stirring, the water mixture was heated to 140° F. and added to the petrolatum preparation in a container. While stirring continued the mixture was cooled to 100° F. then the thyme oil was added and the mixture further cooled to 60°–80° F. for filling. The formulation thus prepared was found to provide a superior topical antiinflammatory product.

Herpes zoster (shingles) is an acute inflammatory disease of the cerebral ganglia and ganglia of the posterior nerve roots, caused by the virus of chicken pox. It is characterized by groups of small vesicles on inflammatory bases occurring in cutaneous areas supplied by certain nerve trunks, and associated with neuralgic pain.

Severe clinical herpes zoster is generally not helped by treatment with presently available antiviral/antiinflammatory medications.

EXAMPLE 32

A number of herpes zoster patients were treated by Sidney Peerless, M. D. of E.N.T. Associates, 3131 Harvey Avenue, Cincinnati Ohio 45229. The treatment was carried out after failure of conventional medication, and comprised treatment with a composition according to the present invention comprising the LYCODERM®/Hydrocortisone Acetate formulation shown above in Example 31.

Patient 1: This patient had shingles of 4 weeks duration, herpes of the right face and forehead. Symptoms: severe pain, breaking out pustules, and redness. Previous treatment: Zovirex capsules, Zovirex ointment, and antibiotics did not help. The patient was placed on LYCODERM®/Hydrocortisone Acetate ointment of Example 31 applied 2–4 times per day to the affected areas. In 3 days the patient showed marked improvement, especially in the pustules and also in the pain threshold. Within 10 days the lesions were improved and the patient felt much better symptomatically.

Patent 2: The patient had severe shingles in the cervical area going into the lower portion of the jaw and into the neck characterized by pustules, severe pain and erythema. Under previous treatment by a dermatologist he had received steroids systemically and Zovirax ointment. After having the disease for three weeks he came to see Dr. Peerless in desperation, because of the severe pain he experienced. The patient also had herpes lesions in his throat. He was placed on the LYCD/Steroid combination ointment of Example 31. After 10 days of treatment the entire facial and neck lesions were gone. There was a marked diminution of pain and need for Demerol, and his general condition improved greatly.

Patient 3: The patient had severe shingles involving the right posterior leg and up to the dorsum of the foot. Under the care of another physician the patient had received steroids, antibiotics systemically, and an antibiotic ointment, Polysporin, applied to the lesions without improvement. The patient came to see Dr. Peerless also in desperation. She was placed on the LYCD/steroid combination ointment of Example 31. After three weeks the lesions were almost completely cleared. The pain factor was gone. The patient was able to wear her shoe and showed overall marked improvement.

Patient 4: This patient had shingles of the lower lumbar area along the nerve root with large pustules, erythema and almost uncontrollable pain. He had been on pain medicine and Zovirax. He had also been given systemic antibiotics and steroids with very little improvement. The patient was placed on the LYCODERM®/Hydrocortisone Acetate ointment of Example 31. In 48 hours his condition improved markedly, especially in reduction of pain. After another 4–5 days on the medication the herpetic lesions were almost completely under control, and medication was continued for another week. Three weeks after stopping the medication, the patient had a recurrence of the herpes. Readministration of the LYCD/steroid ointment of Example 31 for two weeks again brought the herpes under control, and the patient has remained well.

EXAMPLE 33

A formulation was analogously prepared in which the hydrocortisone acetate concentration was reduced to 0.1%. This formulation was found to enhance the anti-erythema, wound-healing properties of the combination product.

EXAMPLE 34

Alternatively, LYCD at levels of 200 to 1800 units SRF per ounce (approximately 0.1% to 0.8%) are added to conventional formulations (creams, lotions, ointments, gels, etc.) of compatible topical adrenocorticoid formulations which are used in concentrations of 0.01% to 1.0% to produce synergistic therapeutic compositions providing more effective medication for the same indications presently approved by the FDA.

A representative listing of Topical Adrenocorticoids which may be used in formulating compositions according to the present invention maybe found in the U.S. Pharmacopeial Convention 1986 publication "THE PHYSICIANS' AND PHARMACISTS' GUIDE TO YOUR MEDICINES", published by Ballantine Books, N.Y. N.Y.

EXAMPLE 35

More particularly, the addition of 0.25% hydrocortisone acetate to the LYCODERM® formulation containing 1000 units of LYCD per ounce of ointment (approximately 0.50%) results in a topical antiinflammatory medicinal composition with greater activity and efficacy than is presently available in any topical steroid product licensed by the U.S. FDA for OTC (over the counter) use.

ANTI-SKIN WRINKLING COMPOSITIONS

EXAMPLE 36

Skin wrinkling is accelerated by deficiencies in collagen synthesis/metabolism. Vitamin A acid (all-trans retinoic acid) is used as a topical preparation to slow or reverse the process of wrinkling. However, its use is limited by concentration related toxicity. According to the present invention LYCD compositions synergistically augment the anti-wrinkling actions of topical retinoic acid with no increase in toxicity. Thus the LYCODERM® formulation previously described is prepared using 1000 units of SRF per ounce (ca 0.5% LYCD) and 0.25% of vitamin A acid to provide a topical ointment composition synergistically more effective than retinoic acid in ameliorating the skin wrinkling process, including photo-aged skin.

EXAMPLE 37

Alternatively, presently used cream (0.1%), gel (0.025%), or liquid (0.05%) Vitamin A acid formulations are augmented with 0.5% of LYCD (about 1000 units SRF per ounce to provide synergistically more effective anti-wrinkling compositions. Additionally, these novel compositions are beneficial in treating ichthyosis, actinic keratosis and other hyperkeratotic conditions.

LYCD may also be combined with other retinoic acid congeners, known collectively as retinoids, which are also useful topical anti-wrinkling agents to produce new compositions as covered by the present invention. A number of these epidermally acting retinoids are described, for instance, in the special issue supplement to The Journal of the American Academy of Dermatology (Volume 15, No. 4, Part 4, October 1986 entitled "TOPICAL RETINOIDS: AN UPDATE".

HAIR GROWTH STIMULATION COMPOSITIONS

Few effective agents are currently available for stimulation of hair growth. Only one topical preparation, a 2% solution of minoxidol, manufactured and marketed by the Upjohn Company, Kalamazoo, Mich., is presently approved by the Food and Drug Administration as a pharmaceutical preparation for the treatment of male pattern baldness (alopecia androgenica) of the vertex of the scalp. At least four months of continuous use is generally required before evidence of hair growth can be seen. The historical development of topical treatments for alopecia is more fully set forth in U.S. Pat. Nos. 4,139, 619 and 4,596,812 which are herein incorporated by reference.

It is an additional objective of the present invention to provide novel and effective treatments for male pattern baldness by the application of topical pharmaceutical compositions incorporating LYCD at the 0.1% to 3.0% level in pharmaceutically acceptable formulations (solutions, creams, gels, ointments, etc.).

EXAMPLE 38

The following LYCD solution was prepared containing 2000 units of SRF per ounce:

| | |
|---|---|
| LYCD/SRF | 1.0% w/v |
| Alcohol | 55.0% w/v |
| Oleyl alcohol | 5.0% w/v |
| Propylene glycol | to 100% |

When applied to the total affected are of the scalp of balding males twice daily for four months, evidence of hair regrowth is observed.

EXAMPLE 39

The following cream formulation of LYCD is also useful for promoting hair growth. The cream contains (per 100 grams):

| | |
|---|---|
| LYCD/SRF | 5250 units |
| Dimethicone | 5.0 g |
| D-pantheol | 4.0 g |
| Benzalkonium Chloride | 0.1 g |
| A water washable cream base | to 100 g |

EXAMPLE 40

For some individuals, another effective composition for treating male pattern alopecia combines LYCODERM® ointment and very low dose hydrocortisone acetate, formulated as follows:

| Ingredient | per 100 parts by wt. |
|---|---|
| Polysorbate 80 | 1.0 |
| Hydrocortisone Acetate | 0.1 |

-continued

| Ingredient | per 100 parts by wt. |
|---|---|
| Phenyl Mercuric Nitrate | 0.01 |
| Live Yeast Cell Derivative (LYCD/SRF, 2000 units/oz.) (approximate) | 1.0 |
| Deionized water | 2.0 |
| Beeswax (white) | 4.0 |
| Lanolin | 4.0 |
| Petrolatum | 84.8 |
| Shark Liver Oil | 3.0 |
| Thyme Oil | 0.1 |

PROCEDURE

The first three ingredients were combined and mixed well. The LYCD was dissolved in water, added to the first group and again mixed well. The third group of ingredients were added separately to a clean container and heated to 160° F. with good mixing. With continued stirring, the water solution was heated to 140° F. and added to the petrolatum/lanolin/beeswax mixture. Stirring continued as the total preparation was allowed to cool to 100° F. Then the thyme oil was stirred in and the mixture further cooled to 60°–80° F. for filling.

EXAMPLE 41

Combinations of LYCD with low doses of Minoxidol or retinoic acid also provide synergistic compositions for treating alopecia androgenica. Advantageously, 0.5% of LYCD is formulated with 1.0% minoxidol solution or with 0.1% of vitamin A acid to provide more effective hair growth compositions, although application for four months may still be required before evidence of hair regrowth is observed.

COMPOSITIONS FOR USE IN OPHTHALMOLOGY

EXAMPLE 42

A 1% to 10% solution of LYCD, in a pharmaceutically acceptable ophthalmic formulation provides a useful composition for the treatment of various eye problems and accelerates corneal epithelial regeneration and the healing of stromal incisions following corneal transplant surgery. More particularly, a 5% solution of LYCD is useful for the acceleration of corneal epithelial regeneration and the healing of stromal tissue in the condition of non-healing corneal defects.

Formulated in combination with low doses of a fibronectin or a laminin (one to 100 nanograms per ml.) LYCD is synergistically more effective in treating Dry Eye, Corneal Incisions, Recurrent Corneal Erosions, and Non-healing Corneal Defects.

EXAMPLE 43

For the treatment of ocular viral infections, such as, for instance, keratitis due to Herpes simplex virus, the 5% solution of LYCD, in a pharmaceutically acceptable ophthalmic formulation is augmented with an antiviral agent (i.e. 1% trifuridine or acyclovir) and 0.5% hydrocortisone (as its water soluble ester).

The compositions of the present invention comprising LYCD in combination with other topically active medicinal ingredients have many advantages over conventional products. The presence of the LYCD in the compositions provides a synergistic effect which makes the conventional materials more effective and permits less of the conventional ingredients to be used while still achieving the same results.

The compositions of the present invention contain, in addition to LYCD and the other pharmaceutically active ingredient, a carrier suitable for rendering the composition as a formulation to be used for topical applications. In one method for forming the compositions of the present invention the carrier is provided by the LYCODERM®. In another method the carrier is provided by the commercial form of the other active ingredient. Alternatively, a suitable carrier known in the art may be added to both the LYCD and the other active ingredient. In all examples above the indicated percent content of the stated ingredients is based on the weight of the total ingredients, the LYCD, the other pharmaceutically active ingredient, and the carrier.

The herein described new topical compositions and methods of treatment for a variety of skin conditions are equally applicable to veterinary problems, that is, the treatment of farm animals as well as domestic pets.

Although the invention has been described in connection with specific embodiments thereof, it is evident that many alternatives, modifications, and variations will be apparent to those skilled in the art in the light of the foregoing description. Accordingly, it is intended to embrace all such alternatives, modifications and variations within the spirit and scope of the invention as defined by the appended claims.

Invention is claimed as follows:

1. A topical composition for the treatment of multiple actinic keratoses, comprising, in admixture with a pharmaceutically acceptable topical carrier, fluorouracil, and from about 0.1% to about 3% by weight of said composition of Live Yeast Cell Derivative (LYCD), said fluorouracil being present in an amount effective to treat the multiple actinic keratoses of the skin.

2. A topical composition according to claim 1, wherein said fluorouracil is present in an amount of about 0.5% by weight, and said Live Yeast Cell Derivative is present in an amount of about 0.5% by weight.

3. A method for treating multiple actinic keratoses of the skin of a human being, which comprises topically applying to said human being a composition comprising, in admixture with a pharmaceutically acceptable topical carrier, fluorouracil, and from about 0.1% to about 3% by weight of said composition of Live Yeast Cell Derivative (LYCD), said fluorouracil being present in an amount effective to treat the multiple keratoses of the skin.

4. A method according to claim 3, wherein said fluorouracil is present in an amount of about 0.5% by weight, and said Live Yeast Cell Derivative is present in an amount of about 0.5% by weight.

* * * * *